(12) United States Patent
Roelant

(10) Patent No.: US 6,171,809 B1
(45) Date of Patent: *Jan. 9, 2001

(54) METHOD AND COMPOSITIONS FOR DETECTING LUCIFERASE BIOLOGICAL SAMPLES

(75) Inventor: Christiaan Roelant, Leuven (BE)

(73) Assignee: Packard Instrument Company, Downers Grove, IL (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/015,090

(22) Filed: Jan. 29, 1998

(51) Int. Cl.[7] ............................. C12Q 1/66; C12N 9/99; C12N 9/02
(52) U.S. Cl. .......................... 435/8; 435/184; 435/189
(58) Field of Search ...................... 435/8, 4, 184, 435/968, 963, 810, 189; 436/166, 172

(56) References Cited

U.S. PATENT DOCUMENTS

| | | | |
|---|---|---|---|
| 4,286,057 | 8/1981 | Wulff et al. | 435/8 |
| 4,665,022 | 5/1987 | Schaeffer et al. | 435/7 |
| 5,292,658 | 3/1994 | Cormier et al. | 435/252.33 |
| 5,418,155 | 5/1995 | Cormier et al. | 435/189 |
| 5,474,897 | 12/1995 | Weiss et al. | 435/6 |
| 5,618,682 | 4/1997 | Scheirer | 435/8 |
| 5,641,641 | 6/1997 | Wood | 435/8 |
| 5,650,289 | 7/1997 | Wood | 435/8 |
| 5,744,320 | * 4/1998 | Sherf et al. | 435/8 |

FOREIGN PATENT DOCUMENTS

| | | | |
|---|---|---|---|
| 0 610 937 A1 | * 8/1994 | (EP) | C12Q/1/66 |
| WO 96/40988 | 12/1996 | (WO) | C12Q/1/66 |

* cited by examiner

Primary Examiner—Ardin H. Marschel
Assistant Examiner—Marjorie A. Moran
(74) Attorney, Agent, or Firm—Jenkens & Gilchrist

(57) ABSTRACT

The presence of renilla luciferase alone or both renilla luciferase and firefly luciferase is detected by adding reagent mixture(s) to a biological sample and producing glow luminescence having a duration of at least an hour. In producing luminescence from renilla luciferase alone, a reagent is added comprising coelenterazine, and dithiothreitol (DTT) and EDTA, or functional equivalents of DTT and EDTA. Luminescence from samples containing both firefly luciferase and renilla luciferase is produced by first adding a reagent comprising firefly luciferin, ATP, co-factors necessary for firefly luciferase activity (e.g., $Ca^{+2}$ and $Mg^{+2}$), dithiothreitol (DTT) or functional equivalents thereof, and AMP. Following measurement of the firefly luciferase, coelenterazine and EDTA, or functional equivalents of EDTA, are added, and the luminescence produced by renilla luciferase is measured.

18 Claims, 2 Drawing Sheets

METHOD AND COMPOSITIONS FOR DETECTING LUCIFERASE BIOLOGICAL SAMPLES

BACKGROUND OF THE INVENTION

This invention relates to the use of luminescence in the analysis of biological materials. More particularly, it relates to methods involving reporter gene techniques in which cells are expressed containing a luciferase and then detected by reactions which produce luminescence.

Luciferases are found in a variety of organisms, including fireflies, photobacteria, jellyfish, and sea pansies, among others. Luciferases may be used to measure reporter genes. In this technology, a reporter gene, such as a luciferase encoding polynucleotide, is used as an indicator for the transcription and translation of a gene in a cellular expression system. The reporter gene is operatively linked to a promoter that is recognized by the cellular expression system. In a typical reporter gene assay, a DNA vector containing the reporter gene is transfected into a cell capable of expressing the reporter gene. After sufficient time has passed for the expression of the reporter gene, the cellular membrane is disrupted to release the expressed gene product. The necessary reagents are then added to permit measurement of the enzyme activity of the reporter gene. In the case where a luciferase is used as the reporter gene, the photons of light produced by oxidation of a substrate called a luciferin are measured.

While the most common luciferase used in analysis by luminescence is firefly luciferase, other luciferases may be used. One such luciferase is renilla luciferase, which is derived from sea pansies, a marine coelenterate of the class anthozoans. The present invention is related to a method of determining the presence of renilla luciferase, either alone or in the presence of firefly luciferase. Heretofore, the use of renilla luciferase as a reporter has been limited by the short period of light generation, as also had been the case with firefly luciferase.

In U.S. Pat. No. 5,618,682, assigned to Packard Instrument Company, it was shown that through the use of certain reagent compositions, the brief release of light ("a flash") from firefly luciferase could be extended for many hours ("a glow"). The advantage of extending the time during which light is released is that it becomes possible to carry out screening of multiple samples simultaneously, which is not feasible if the flash of light lasts only a few seconds or minutes. Such reagent compositions have been very successful commercially under the trademark LucLite™.

The release of light by bioluminescence with firefly luciferase involves the oxidation of a substrate, i.e., a luciferin, in the presence of adenosine triphosphate (ATP) and oxygen to produce adenosine monophosphate (AMP), pyrophosphate, and carbon dioxide.

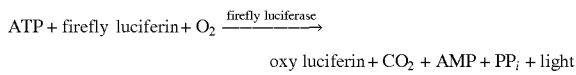

$$ATP + \text{firefly luciferin} + O_2 \xrightarrow{\text{firefly luciferase}} \text{oxy luciferin} + CO_2 + AMP + PP_i + \text{light}$$

This reaction is illustrated in U.S. Pat. No. 4,286,057 in which a method is disclosed for measuring creatine kinase via the reaction of adenosine diphosphate with creatine phosphate which is catalyzed by creatine kinase and produces ATP. The product ATP is measured by the firefly luminescence reaction and, thus indirectly, the activity of creatine kinase. An increase of the light duration was found to result from adding the reaction product AMP, although the patentees in the '057 patent did not indicate that they obtained a glow time of several hours, as did the patentee in the '682 patent.

The reaction of renilla luciferase differs from that of firefly luciferase in that the substrate is a different molecule, coelenterazine, rather than the firefly luciferin, and only oxygen is involved.

$$\text{coelenterazine} + O_2 \xrightarrow{\text{renilla luciferase}} \text{oxy coelenterazine} + CO_2 + \text{light}$$

Carbon dioxide is produced as with firefly luciferase, but neither ATP nor AMP are required. Thus, the reagents used need not include ATP and AMP as used in the firefly luciferase reaction. It has now been discovered, however, that when the reagents used in the firefly luciferase reaction taught in the '682 patent are present when renilla luciferase is being detected, the extended glow time obtained with firefly luciferase is present with renilla luciferase as well. At the same time, the amount of light produced is increased by a factor of ten relative to that of firefly luciferase in a dual assay system.

In one commercially available system from Promega Corporation, a dual reporter technique is used in which an assay is made first with firefly luciferase, after which the first reaction is quenched and a second assay is made using renilla luciferase. The total time required for both assays is said to be about 30 seconds. Thus, the method does not depend on maintaining a long glow period, and the short time is considered an advantage of the system. For multiple screening tests using many samples simultaneously, however, such a short period is not desirable. Instead, much longer glow times are advantageous. The present invention is intended to provide a method for accomplishing that objective.

In WO 96/40988, assigned to Promega Corporation, both single and dual reporter assays are discussed. They are characterized by the use of quenching agents to prevent crosstalk between adjacent sample cells in a multiple cell sample plate or, in dual assays, to stop a first reaction so that a second reaction can be carried out. It is said that by the use of this method, more accurate single assays can be achieved and that dual assays can be carried out in a single sample cell. According to the patentees, it is possible to carry out a dual assay in about 30 seconds. Thus, it appears that the extended glow period desired by the present inventors was not present in either of the two reactions, nor was it considered desirable.

SUMMARY OF THE INVENTION

In one aspect, the present invention provides methods for assaying biological samples for the presence of firefly luciferase and renilla luciferase together or for renilla luciferase alone. A reagent composition is added which will include compounds selected to produce an extended glow rather than flash luminescence. For detection of firefly luciferase, firefly luciferin, ATP and AMP are required. For detection of renilla luciferase, the corresponding luciferin, coelenterazine, is required. In addition, the composition may include free radical scavengers such as dithiothreitol (DTT), chelating agents such as ethylene diaminetetraacetic acid (EDTA), detergents such as Triton® N-101 (nonylphenoxypolyethoxyethanol), buffers such as HEPES, N-[2-hydroxyethyl] piperazine-$N^1$-[2-ethane sulfonic acid], and protease inhibitors such as phenylacetic acid (PAA) and oxalic acid (OA).

In one embodiment, a sample suspected to contain renilla luciferase is mixed with a reagent mixture containing coelenterazine, as a free radical scavenger, DTT, and, as a chelating agent, EDTA, or functional equivalents of DTT and EDTA. Optionally, the mixture may include one or more detergents, buffers, and protease inhibitors. The luminescence is measured by methods familiar to those skilled in the art, such as the TopCount™ Microplate Scintillation and Luminescence Counter available from Packard Instrument Company, Inc., Downers Grove, Ill. In a preferred embodiment, each 100 mL of the reagent mixture contains about 0.2–30 mg of coelenterazine, about 200–2,000 mg of DTT, and about 0.05–100 mg of EDTA. The coelenterazine may be native coelenterazine or an analogue, such as m-, e-, v- or f-coelenterazine. The reagent optionally may contain a protease inhibitor such as phenylacetic acid (PAA) or oxalic acid (OA) and a detergent such as nonylphenoxypolyethoxyethanol.

In another aspect, the invention is a method for detecting the presence of both firefly and renilla luciferases in a single sample. The firefly luciferase is measured by adding to the sample a reagent mixture containing firefly luciferin, adenosine triphosphate (ATP), co-factors necessary for firefly luciferase activity such as $Mg^{+2}$ and $Ca^{+2}$, dithiothreitol (DTT) or functional equivalents thereof, and adenosine monophosphate (AMP) in amounts selected to produce luminescence having a duration of at least 1 hour and an intensity that varies substantially linearly with time and measuring the luminescence which is produced. Optionally, the mixture may is include one or more detergents, buffers, and protease inhibitors. Following the measurement of the amount of firefly luciferase in the sample, a buffer solution containing coelenterazine and EDTA or its functional equivalent is added. The luminescence produced is measured as before and related to the amount of renilla luciferase present in the sample. The coelenterazine may be native coelenterazine or an analogue, such as m-, e-, v-, or f-coelenterazine. EDTA is used in a molarity between about 10 $\mu$M and 10 mM, and the pH is maintained between 6 and 8.5. Preferably, the coelenterazine is present in a concentration of 2–5 $\mu$M in a 1–10 mM EDTA buffer solution having a pH between 7.2–8.0.

In another aspect, the invention relates to reagent compositions and test kits for carrying out the methods of the invention. In one application, the invention is an assay kit for detection of G-protein coupled reactions using the dual glow signal produced by firefly luciferase and renilla luciferase. In another aspect, the assay kit may be used for the detection of two-signal transduction pathways within the same cell, for example, to screen clones with selective agonists. Alternatively, the assay kit may be used to assay compounds or drugs against two receptors plated in the same well of a microtiter plate or applied to a solid support.

DESCRIPTION OF ILLUSTRATIVE EMBODIMENTS

Luminescence Reactions

Figure 1:
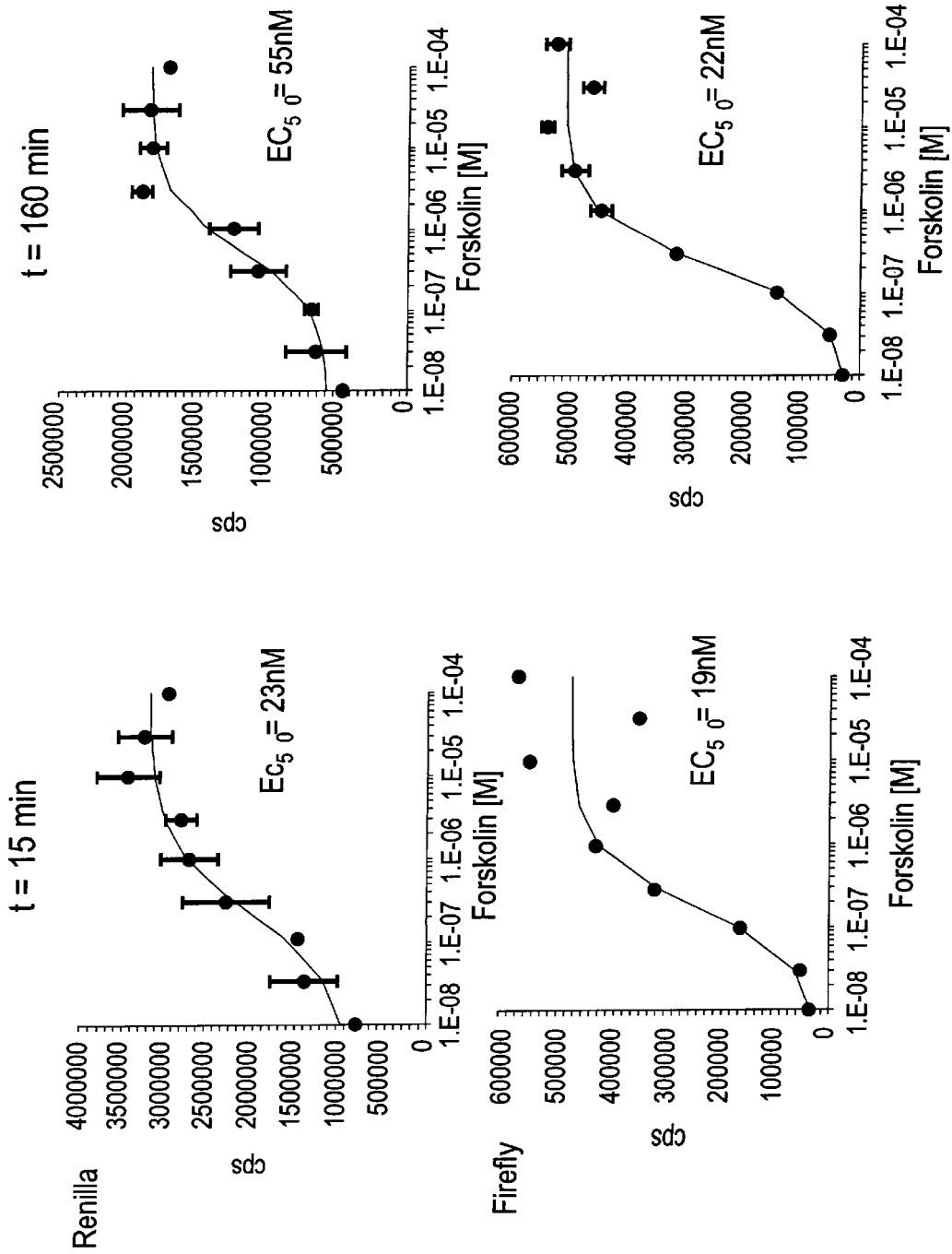
FIG. 1 illustrates the renilla and firefly luminescence of cells stimulated with forskolin.

The luminescence associated with firefly luciferase involves a reaction in which a substrate, luciferin, reacts with ATP and oxygen in the presence of a co-factor such as $Mg^{+2}$ to produce an oxidized form of the luciferin, AMP, pyrophosphate, carbon dioxide, and light. The amount of light is measured to determine the amount of luciferase present. It is typical of this reaction that the light appears as a brief flash. While it can be measured, it is not convenient to do so in many instances where multiple samples are being screened simultaneously. In U.S. Pat. No. 5,618, 682, Scheirer disclosed an optimum composition for the reaction mixture which has the benefit of extending the flash of light so that it becomes a glow which lasts for an hour or more. This composition is commercially available under the trademark LucLite™ from the Packard Instrument Company and has achieved considerable success. The reaction mixture includes AMP and other compounds which provide the extended glow period, in particular, the free radical scavenger dithiothreitol (DTT), the chelating agent ethylenediaminetetraacetic acid (EDTA), and protease inhibitors such as phenylacetic acid or oxalic acid. Functional equivalents of these compounds may be used. A detergent may be present if cells are to be lysed, also a buffering agent such as HEPES may be used. This composition has now been found to produce an extended glow period when a dual assay is carried out, with the first reaction being catalyzed by the firefly luciferase and the second catalyzed by renilla luciferase.

The luciferin compound which serves as the substrate for the light producing reaction catalyzed by renilla luciferase differs in its chemical structure from the luciferin which reacts under the influence of firefly luciferase. The common name for this compound is coelenterazine. It also oxidizes to produce light and carbon dioxide. However, it does not require the presence of ATP and does not produce AMP and pyrophosphate as co-products. Thus, one would not predict that the reaction mixture disclosed in the Scheirer patent would have a beneficial effect on the light produced in the reaction of coelenterazine with oxygen catalyzed by renilla luciferase. The present inventor has found that it is possible to carry out the reaction of coelenterazine with oxygen in the presence of such a composition and that an extended glow period of at least one hour is achieved. Furthermore, the intensity of the glow varies substantially linearly with time. This is useful when a dual assay is carried out. However, all the composition is not needed if only the reaction of coelenterazine with oxygen is to be carried out to determine the presence of renifla luciferase. In such a case, an extended glow period can be obtained by including only certain effective amounts of DTT and EDTA, or their functional equivalents, as will be seen below.

Extending the Period for Light Emission

As suggested above, the period during which light is emitted in the oxidation is reaction catalyzed by firefly luciferase can be extended for many hours and with a linear decay characteristic, thus permitting analysis of many samples in a multiwell sample plate, such as the ViewPlate™ available from the Packard Instrument Company. While this appears likely to cause undesirable crosstalk between the sample cells, as suggested in the Promega patent application discussed above, it should be noted that it is also feasible (and typical in commercial instruments) for corrections to be made to remove crosstalk effects from the results.

To samples containing an expressed gene product including firefly luciferase, is added a reagent mixture, an example of which may include for each 100 ml:

| | |
|---|---|
| firefly luciferin | about 0.2–30 mg |
| DTT | about 200–2000 mg |
| EDTA | about 0.05–100 mg |
| AMP | about 0.2–30 mg |
| ATP | about 10–300 mg |
| PAA (optional) | about 1–6 mg |
| OA (optional) | about 0.5–1 mg |
| HEPES (optional) | about 50–1000 mg |
| Triton N-101 (optional) | about 50–100 mg (nonylphenoxypolyethoxyethanol) |

Of these, the presence of DTT and AMP are considered the most important in providing an extended glow period. While each of these compounds has been reported in the literature, the composition of the '682 patent was unique in that it made possible an extended glow period of at least one hour and a substantially linear light output not previously available. Even longer glow periods are possible.

Dithiothreitol (DTT) is a preferred radical scavenger. Others which are considered functional equivalents include hydrosulphydryl compounds such as dithioerythritol, glutathione, cysteine, —SH containing amino acids, coenzyme A, beta mercaptorethanol and the like. Such compounds increase the duration of detectable photon emission and, as shown in the '682 patent, DTT can actually increase the light emitted.

Ethylenediaminetetraacetic acid (EDTA) is a preferred chelating agent. Others which are considered functional equivalents include ethyleneglycol-bis (β-aminoethylether), and $N,N,N^1,N^1$-tetraacetic acid (EGTA), among others. Such compounds tend to bind $Mg^{+2}$, $Ca^{+2}$, and other divalent cations which are necessary co-factors for firefly luciferase activity. The amount of EDTA or equivalent used in the present invention is significantly less than suggested by Promega's patent application discussed above, in which it is shown that large amounts of EDTA can quench the firefly luciferase reaction.

Phenylacetic acid (PAA) and oxalic acid (OA) are the preferred protease inhibitors. Others considered functional equivalents includes monensine, acetyl phenylalamine, leupeptine, ammonium chloride, and oprotinin. Such compounds limit the deactivation of luciferases by endogenous proteases with the cell lysates and thereby lengthen the time when light is emitted.

Detergents such as nonylphenoxypolyethoxyethanol are used to lyse cells. They may be used in reagents of the invention, although if the luciferase is free, rather than expressed from cells, detergents are not necessary.

The pH of the sample is a factor in the oxidation of luciferins. Consequently, buffering agents, such as HEPES, N-[2-hydroxyethyl] piperazine-$N^1$-[2-ethenesulfonic acid], may be included to maintain the pH within the desired range.

EXAMPLES

A kit for the sequential detection of firefly luciferase and renilla luciferase was prepared which consisted of a firefly luciferase assay reagent and a renilla luciferase assay reagent.

The firefly luciferase reagent consisted of AMP, EDTA, firefly luciferin, ATP, DTT, phenylacetic acid and oxalic acid as originally described in U.S. Pat. No. 5,618,682.

The renilla luciferase reagent consisted of 5 μM of coelenterazine in 2 mM EDTA buffer with a pH 7.5.

Stable mammalian cell lines transfected with c-AMP responsive reporter genes containing either the firefly or renilla luciferase reporter proteins (CRE-firefly and CRE-ren) were generated.

Next, the CRE-firefly cells were further transfected with the human vasopressin V2 receptor and CRE-ren cells were transfected with the human beta-2 adrenoceptor. These receptors are members of the super family of G-protein coupled receptors which interact with the stimulatory G-protein alpha unit.

Firefly luciferase and/or renilla luciferase producing CHO (Chinese hamster ovary) cells are cultured in tissue culture flasks and grown to 90% confluency. Twenty-four hours before the assay, the cells are quiesced in serum-free medium containing 1 mg/ml BSA (bovine serum albumin). Immediately prior to the assay, cells are removed with HBSS/EDTA (Hanks balanced salt solution containing EDTA), centrifuged and resuspended in 10 ml phenol red-free and serum-free medium supplemented with 1 mg/ml BSA. Next, the cells are plated into a 96 well microtiter plate at 90 μl/well and returned to the incubator. After 1 hour, 10 μl of the test compound, made up in either water or phenol red-free medium, is added. The microplates then are further incubated for 4 hours. Finally, the firefly luciferase detection reagent is made up and 100 μl of this detection solution is added to each well. After 10 minutes, the microplate is counted for firefly luciferase activity. Next, to each well, 100 μl/well of 5 μM of coelenterazine in 2 mM EDTA buffer solution is added. The plate is left for 15 minutes in the dark and then counted for renilla luciferase activity.

Example 1
Stability of the Renilla Luciferase Luminescence

CRE-ren cells were stimulated with 10 μM forskolin, a compound which directly activates adenylcyclase to cause an increase in the level of intercellular cAMP. To examine the nature of the forskolin response, CRE-firefly and CRE-ren cells were mixed and plated into individual wells of a black 96-well ViewPlate™ (Packard Instrument Company). A forskolin dose response curve was constructed and cells were assayed using either the firefly detection reagent or the renilla luciferase detection reagent. The assay plates were counted in a TopCount™ Luminescence Counter (Packard Instrument Company) at 15 or 160 minutes after reagent addition. The EC50 (Effective Concentration to produce 50% activity) for forskolin activation of the cAMP reporter genes was similar at all time points and with both the renilla and firefly luciferase reporters. As shown in FIG. 1, the nature of the firefly luminescence was identical at 15 and 160 minutes after reagent addition, demonstrating the stability of the firefly luciferase detection reagent. Upon addition of the renilla detection reagent to these plates, the firefly luciferase response becomes partially quenched and renilla luciferase response is revealed. While the renilla luciferase luminometric response decays from $3.5 \times 10^6$ at 15 minutes to $1.8 \times 10^6$ at 160 minutes, the EC50 for forskolin stimulation of adenyl cyclase remains similar. Furthermore, renilla luminescence generated using the composition of this invention, is 10-fold brighter than the firefly luciferase generated light signal.

Figure 2:
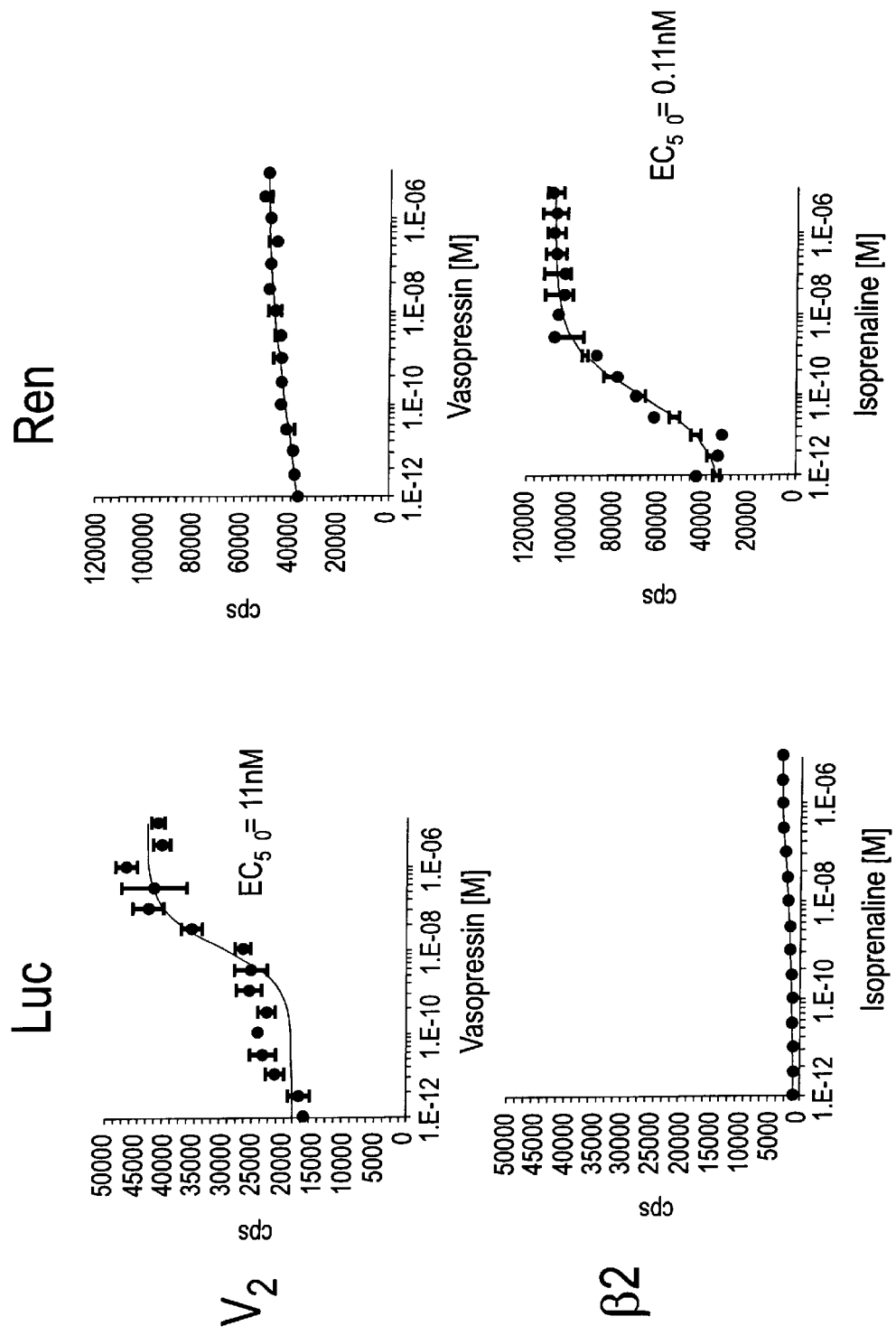
FIG. 2 illustrates the renilla and firefly luminescence of cells stimulated with isoprenaline and vasopressin.

Example 2
Use of the Firefly Luciferase and Renilla Luciferase Detection Reagents to Characterize Receptor Signalling CRE/firefly/V2 and CRE/ren/beta2 cells were mixed and plated into individual wells of a black 96-well ViewPlate. Dose response curves to the V2 agonist vasopressin and the beta2 agonist isoprenaline were constructed using firefly luciferase to determine isoprenaline activity. Following the addition of the firefly luciferase detection reagent, vasopressin was seen to activate the V2 receptor with an EC50 of 11 nM. As shown in FIG. 2, vasopressin did not stimulate renilla luminescence. Following the subsequent addition of renilla detection reagent to the same cells, the response curve to vasopressin was flattened and a dose response curve to isoprenaline was revealed with an EC50 of 0.11 nM.

Example 3

Compound Screening Using Combined Glow Luminometric Measurement of Firefly Luciferase and Renilla Luciferase CRE/firefly/V2 and CRE/ren/beta2 cells were mixed and plated into individual wells of a black 96-well ViewPlate and a range of compounds were applied to the cells. Following the assay with the firefly luciferase detection reagent, responses were obtained with the V2 receptor agonists vasopressin and desmopressin. As expected, a firefly luciferase response was obtained with forskolin and also with thyro-calcitonin (CHO cells express an endogenous calcitonin receptor). Following the addition of renilla luciferase detection reagent, the luminescence signal generated by vasopressin and desmopressin was not significantly above basal. A luminescent signal was maintained with forskolin and thyro-calcitonin and was now seen following stimulation with isoprenaline. Hence, the assay correctly demonstrates that vasopressin and desmopressin are agonists at the V2 receptor, isoprenaline is a beta2-adrenoceptor agonist and that forskolin and thyro-calcitonin act on CHO cells to generate an endogenous response. Glutamate, nociceptin and serotonin are not agonists active at these cells.

What is claimed is:

1. A method for detecting the presence of both firefly luciferase and renilla luciferase in a sample by measuring the luminescence of said sample comprising:
   (a) mixing said sample with a first reagent mixture containing firefly luciferin, adenosine triphosphate (ATP), co-factors necessary for firefly luciferase activity, dithiothreitol (DTT) or functional equivalents thereof, and adenosine monophosphate (AMP), the amounts of said firefly luciferin, ATP, co-factors, DTT or equivalent, and AMP being sufficient to produce luminescence having a duration of at least one hour and an intensity that varies substantially linearly with time; and
   (b) measuring the luminescence produced by the mixture of the sample and first reagent mixture of (a);
   (c) adding a second reagent mixture comprising a buffer solution containing coelenterazine and, as a free radical scavenger, EDTA or functional equivalents thereof, to the mixture resulting from (a) after said measuring of (b) in an amount sufficient to partially quench the luminescence measured in (b);
   (d) measuring the luminescence produced by the addition of (c), said luminescence having a greater intensity than measured in (b) an extended glow period of at least one hour and which varies substantially linearly with time.

2. The method of claim 1, wherein for each 100 ml, the first reagent mixture contains about 0.2–30 mg of firefly luciferin, about 200–2000 mg of DTT, about 0.2–30 mg of AMP, and about 10–300 mg of ATP.

3. The method of claim 1, wherein said coelenterazine is native coelenterazine or an analog thereof.

4. The method of claim 1, wherein said buffer solution contains about 10 μM to about 10 mM of EDTA and has a pH of about 6–8.5.

5. The method of claim 1, wherein said sample is a sample comprising cells producing firefly luciferase and/or renilla luciferase.

6. The method of claim 5, wherein said first reagent mixture further contains a detergent.

7. The method of claim 6, wherein said detergent is nonylphenoxypolyethoxyethanol.

8. The method of claim 1, wherein said first reagent mixture of (a) further comprises, as a protease inhibitor, phenylacetic acid or oxalic acid, or functional equivalents thereof.

9. The method of claim 1, wherein said first reagent mixture further contains a buffer.

10. The method of claim 9, wherein said buffer is HEPES.

11. An assay kit for detecting firefly luciferase and renilla luciferase in a sample comprising:
   (a) a first reagent mixture for addition to said sample for detecting firefly luciferase activity, said reagent mixture comprising firefly luciferin, ATP, co-factors necessary for firefly luciferase activity, as a free radical scavenger, dithiothreitol (DTT) or functional equivalents thereof, and AMP in amounts sufficient to produce luminescence having a duration of at least 1 hour and an intensity that varies substantially linearly with time; and
   (b) a second reagent mixture for addition to said sample after the activity of firefly luciferase has been detected, said second reagent mixture comprising a buffer solution containing coelenterazine and, as a chelating agent, EDTA or functional equivalents thereof, in amounts sufficient to partially quench the luminescence of (a) and to produce a glow luminescence having a greater intensity than the luminescence of (a) and an extended glow period up to at least one hour which varies substantially linearly with time.

12. The assay kit of claim 11, wherein said coelenterazine is native coelenterazine or an analog thereof.

13. The assay kit of claim 11, wherein said buffer solution contains about 10 μM to about 10 mM of EDTA and has a pH of about 6–8.5.

14. The assay kit of claim 11, wherein said first reagent mixture further comprises, as a protease inhibitor, phenylacetic acid or oxalic acid, or functional equivalents thereof.

15. The assay kit of claim 11, further containing a detergent.

16. The assay kit of claim 15, wherein said detergent is nonylphenoxypolyethoxyethanol.

17. The assay kit of claim 11, further containing a buffer.

18. The assay kit of claim 17, wherein said buffer is HEPES.

* * * * *